United States Patent [19]
Lemelson

[11] Patent Number: 5,995,866
[45] Date of Patent: Nov. 30, 1999

[54] METHOD AND APPARATUS FOR SCANNING AND EVALUATING MATTER

[76] Inventor: Jerome Lemelson, 868 Tyner Way, Incline Village, Nev. 89450

[21] Appl. No.: 08/911,220

[22] Filed: Aug. 15, 1997

Related U.S. Application Data

[62] Division of application No. 08/407,690, Mar. 21, 1995, Pat. No. 5,735,276.

[51] Int. Cl.$^6$ ........................................................ A61B 5/00
[52] U.S. Cl. ........................ 600/476; 600/310; 250/461.2; 356/303
[58] Field of Search ...................................... 600/310, 322, 600/407, 473, 476; 606/3, 10, 11, 12, 13; 250/461.2, 578.1; 356/318, 303; 128/920

[56] References Cited

U.S. PATENT DOCUMENTS

| | | |
|---|---|---|
| 4,758,727 | 7/1988 | Tomei et al. . |
| 4,894,547 | 1/1990 | Leffell et al. . |
| 4,973,848 | 11/1990 | Kolobanov et al. . |
| 5,089,384 | 2/1992 | Hale . |
| 5,110,204 | 5/1992 | Miles et al. . |
| 5,284,149 | 2/1994 | Dhadwal et al. . |
| 5,456,252 | 10/1995 | Vari et al. . |
| 5,464,013 | 11/1995 | Lemelson . |
| 5,474,910 | 12/1995 | Alfano . |
| 5,599,717 | 2/1997 | Vo-Dinh . |
| 5,697,373 | 12/1997 | Richards-Kortum et al. . |
| 5,713,364 | 2/1998 | DeBaryshe et al. . |
| 5,735,276 | 4/1998 | Lemelson . |

Primary Examiner—William E. Kamm
Assistant Examiner—Shawna J. Shaw

[57] ABSTRACT

A system and method for analyzing matter by computer analysis of electrical signals generated by sensing radiation reflected from matter (i.e. tissue, cells, liquid, gaseous or solid particles in a liquid or gas) and/or generated due to fluorescence. In one embodiment, a short pulse of laser radiation is directed at matter also scanned by an electro-optical scanning means to generate image signals. Fluorescent radiation and reflected radiation generating image signals, generate respective variable electrical signals which are computer processed and analyzed to detect and determine the chemical and/or biological composition of the matter. A television camera scans the matter and generates video signals for computer processing and analysis. Simultaneously or sequentially, pulsed laser energy is directed against plural locations of scanned matter, wherein each of such pulses generates a short duration of fluorescent energy in different select portions of the matter under analysis. Fluorescing light is photoelectrically detected generating variable electrical signals for each portion of fluorescing matter, which signals are computer processed and analyzed along with signals output by the television camera to provide information used to intelligibly indicate: (a) composition of such matter, (b) presence of one or more chemical and/or biological agents in such matter, (c) whether the matter is defective or diseased or, (d) a combination of such indications. The liquid may be any body fluids Manipulators are provided to move the TV camera, lasers, sensors and treatment lasers and/or surgical instruments.

24 Claims, 5 Drawing Sheets

METHOD AND APPARATUS FOR SCANNING
AND EVALUATING MATTER

This is a division of application Ser. No. 08/407,690, filed Mar. 21, 1995, now U.S. Pat. No. 5,735,276, issued Apr. 7, 1998.

FIELD OF THE INVENTION

The present invention relates to method and apparatus for analyzing and/or treating matter and more particularly to method and apparatus for such analysis and treatment employing automated computer and laser scanning techniques.

SUMMARY OF THE INVENTION

This invention relates to a system, method and apparatus for detecting and quantizing disease, such as cancer, employing radiation, such a laser radiation, which is directed as a beam or beams to a select portion of the skin or internal tissue of a patient such as via a catheter or instrument, which select portion includes diseased tissue such as cancerous or precancerous cells against or across which the radiation beam is scanned. The radiation beam is so generated and varied during its scanning movement across select tissue and/or as it statically intersects select tissue such as a tumor or a malignancy, that it causes variable fluorescence or spectral radiation to be emitted by the select tissue, cancer or precancerous cells. Photoelectric or optical detection of such spectral radiation results in the generation of variable electrical or optical signals which are computer processed and analyzed in a manner to (a) detect the presence of the disease or cancer and/or precancerous cells, (b) quantize the cancer and/or precancerous cells in terms of their number, distribution and/or the shape and location of the malignancy, (c) determine the type of cancer, (d) determine the stage of the malignancy, and (e) determine the stages of different portions and/or cells of the malignancy or disease.

Forms and operational modes of the invention are noted as follows:

(a) In a first form of the invention, a laser beam is generated by a tunable laser and directed at a first intensity and frequency or wavelength against a select portion of skin. The laser is hand-held or held by a support adjacent to or within a patient. Such laser radiation may also be directed from a (solid state) laser at the end of an elongated part of an instrument such as a laparoscope, catheter or endoscope or along a light pipe defined by an elongated passageway in a tube or optical fiber(s) of such instrument from an external laser or a laser coupled to or defined by such fiber(s), against a select portion of internal tissue such as the wall of a body duct or a lesion or tumor (polyp) formed therein or in tissue adjacent said duct, or other type of diseased tissue from a laser within or external of such elongated part. The intensity and frequency of the first laser radiation is such as to cause all or a portion of the tissue or cells of the tissue or body fluid it irradiates to become excited and fluoresce at a select frequency or wavelength. Such fluorescent radiation (with or without the reflected radiation) is photoelectrically detected by one or more photoelectric cells or photodiodes located adjacent the laser or within the instrument. The resulting electrical or optical signals are computer processed and analyzed to generate first code signals which are modulated with or define first information relative to the cells or tissue so excited. Such first code signals are then employed to intelligibly indicate first information about the fluorescing tissue, such as if it is cancerous or precancerous.

In accordance with such first code signals and/or the program of the computer, control signals are next generated by the computer which are applied to controllably vary the frequency or wavelength and/or the intensity of the laser radiation while it is directed against the same tissue to excite same or cause it to vary the fluorescent or spectral radiation it emits. As such fluorescence radiation is generated and/or so varies when it attains a select frequency or wavelength, it is photoelectrically detected and the resulting signals output by the photoelectric detector are computer processed and analyzed to generate second code signals. The series of code signals so generated are computer analyzed to generate further code signals in one or more analyzing steps, which further code signals may be employed to intelligibly indicate one or more of the variables described above. Fuzzy logic, neural network and/or so-called expert computer subsystems may be employed to effect such analysis and the quantizing of the results.

(b) In a second method, the laser radiation beam described is caused to effect scanning movement with respect to select skin or internal tissue of a patient including at least a portion thereof which is cancerous and/or a precancerous portion. The scanning may be continuous along a select path or group of paths such as spiral or raster paths, and/or stepped from one tumor or tumor portion to the next, or the computer analysis may be effected while the beam is held stationary at one or a series of select locations such as at different small tumors in a select portion of tissue or organ of the patient. The above procedure, wherein the laser beam is continuously and/or intermittently varied in wavelength or frequency and/or in intensity under computer control, is employed while the beam is in scanning movement and/or while it is stopped at such plurality of select locations. The resulting code signals are computer analyzed to quantize the malignancy, tumor or tumors. The codes generated at each step and/or location of the beam may be employed by the computer to controllably vary the wavelength or frequency and intensity of the tunable scanning laser beam during a single scan or during repetitive scans of the same portion or portions of tissue (or body fluid such as blood, lymph fluid, etc.), again employing an expert system, fuzzy logic and/or neural network computer processing. The code signals per se or combined with timing code signals generated during scanning may be employed to locate and indicate the size and shape of the tumor or tumors scanned. Such computerized scanning and spectral analysis may be combined with image analysis techniques to either define, and/or quantize and locate the tumor(s) and determine the stage or stages of the cancer(s) detected and scanned.

(c) In a third computer controlled method, a plurality of lasers are employed to generate and simultaneously or sequentially direct respective laser light beams of different select wavelengths or frequencies (and/or intensities) at the same tissue while such radiation is stationary or in scanning movement. Computerized fluorescence radiation analysis and/or image analysis is effected as above to detect, locate, quantize and determine the state or stage of cancer of the tumor or tumors scanned or the disease under investigation.

(d) In a fourth method, one or more of the tissue scanning techniques set forth are employed to generate quantitative information in the disease or diseased tissue, such as the type of cancer, its stage of development, the size of a tumor or tumors, the location(s) thereof, etc. Such information is analyzed by one or more expert systems, fuzzy logic and/or neural network computers which generate coded control signals. The control signals are employed to control the operations) of one or more motors, solenoids, controls or the like for controlling and operating a treatment system, such as one which applies select amounts of one or more drugs and/or radiation (beams) operable to destroy or cure the disease such as destroy cancer or precancer cells or render same noncancerous.

This invention further relates to a system and method for scanning matter, such as chemical and/or biological matter in liquid or gaseous form or solid particles or matter carried in a liquid or gas, to automatically detect and quantize select matter therein. While a particular and preferred application of the invention is to automatically scan and detect select biological material or elements, such as microbes, viruses and select proteins, chemicals or biochemicals in a mixture of matter, such as body fluid including blood, lymph fluid, saliva, urine and/or other body fluid, the invention may also be employed to scan, detect and separate, selectively irradiate or destroy or otherwise change select biological elements in vivo or in vitro with respect to living animal or plant life, such as a living being, a culture or otherwise confined amount of biological material, a sample of tissue, a single cell sample or group of cells, bacteria, virus, protein or proteins or a mixture thereof which is desired to be biologically engineered, purified, genetically changed or selectively destroyed, To the end of achieving such change, separation or detection of select matter in a sample, batch or flowing stream thereof, a beam or beams of select radiation such as generated by a laser, electron gun and/or other means, is either directed along a single axis and at a moving stream or a moving or stationary sample of matter or is caused to be deflected and thereby controllably scan a stationary quantity of matter or moving matter such as a fluid stream or quantity of matter supported by a moving substrate. The radiation beam is either collimated or narrow enough or focused in a manner to permit it to intersect and react on a domain of matter, such as a select organism, tissue specimen, single cell, bacteria, virus or otherwise formed small quantity of matter which is secured to or forms part of a substrate or is floating on or with a liquid such as blood or other fluid, plant fluid or the like. Thus, during relative scanning movement of the matter or liquid containing same, when the radiation beam intersects such select matter, it may cause a select amount of same or an ingredient therein to fluoresce and emit fluorescent energy of sufficient intensity to be photoelectrically detected by a photoelectric detection means, which is operable to receive such fluorescent energy during the scanning operation and convert same to an electrical signal modulated with information relating to the fluorescent energy received.

In a modified form of the invention, light reflected from a specimen is also photoelectrically detected during scanning and radiation variations therein caused by variations in the reflectivity of the matter scanned, cause corresponding modulations of the electrical signal or signals output by the photoelectric detection means. Such reflections and/or fluorescent-energy-generated detection signals are recorded and/or are computer processed and analyzed immediately and in real time by a computer which is operable to generate control or coded electrical signals which are employed thereafter to effect one or more automatic functions One such function may comprise intelligibly indicating the presence of such select matter. Another function may comprise intelligibly indicating the location or locations of such select matter. A third function may comprise intelligibly indicating the quantity or density of such select matter in the sample or quantity of matter scanned. Another function may comprise intelligibly indicating the presence, quantity or density of a plurality of different types of select matter. Such functions may also be supplemented by the generation of information signals and may be computer processed and analyzed to effect automatic control of signal variable means for reacting on matter scanned, a select portion or portions thereof detected as a result of such scanning to controllably destroy, biologically change and/or separate same from the remaining matter scanned. Changes in, destruction of or separation of select portions of matter, such as select cells in blood or other body fluid, select bacteria or virus or select protein material or chemicals, may be effected by controlling the scanning radiation per se concentrated on the select matter detected, such as by diverting or levitating same or by increasing the intensity thereof, selectively changing (e.g.— continuously or step increasing the frequency and/or wavelength thereof), an auxiliary beam of radiation may be controllably generated and directed at the select matter as a result of the computer analysis of the laser radiation scanned across the select matter.

OBJECTS OF THE INVENTION

Accordingly it is a primary object of this invention to provide a new and improved system and method for scanning and detecting or identifying select matter of a portion of matter containing such select matter and other matter, in mixture, as cellular tissue or otherwise combined.

Another object is to provide automatic means for detecting and indicating the presence of a select chemical and/or biological material, in a sample of matter or in tissue or body fluid of a living being.

Another object is to provide a system and method for automatically separating select elements of matter from a mixture or culture thereof with other matter.

Another object is to provide a system and method for automatically separating select cells, bacteria, viruses, proteins and the like from body fluid such as blood, lymph fluid, urine, saliva or the like.

Another other is to provide a system and method for genetically altering biological material with radiation.

Another object is to provide a method for automatically scanning and genetically altering or engineering select biological material existing in a mixture thereof or in a liquid, using scanning radiation to detect same.

Another object is to provide a system and method for analyzing select matter in a field or sample of such matter by a combination of computerized image analysis of the matter in the field and computerized fluorescence analysis of select amounts of matter in the field scanned wherein both scannings occur simultaneously.

Another object is to provide a system and method for analyzing select matter in a field or sample of such matter by a combination of computerized image analysis of the matter in the field and computerized fluorescence analysis of select amounts of matter in the field scanned wherein both scannings occur sequentially.

Another object is to provide a system and method for analyzing select matter in a field or sample of such matter by a combination of computerized image analysis of the matter in the field and computerized fluorescence analysis of select amounts of matter in the field scanned wherein separate beams of radiation are employed to effect each of the scannings.

Another object is to chemically and/or physically alter or etch semi-solid and solid matter using laser techniques.

DETAILED DESCRIPTION OF THE INVENTION AND PREFERRED EMBODIMENTS THEREOF

Figure 1:
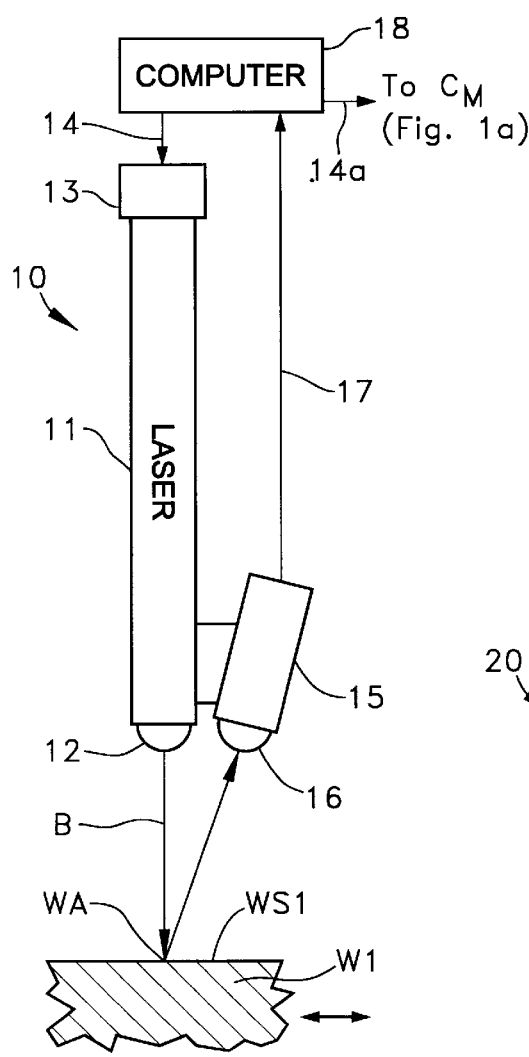
FIGS. 1, 2, 3 and 4 are schematic drawings showing various embodiments for laser beam generation, deflection and sensing.

FIG. 1 shows a portion of an automatic scanning system 10 operable to scan, identify, quantize and/or locate select matter over a scanning field which may be composed of different types of matter such as different molecules, chemicals, cells or a combination thereof and/or other biological matter.

In a preferred form of the invention, automatic computerized scanning of biological matter, tissue, cells, blood or other fluid is performed to detect select biological material over the field scanned, which may contain one or more cancer cells, select proteins or other matter, as well as chemical constituents such as elements, compounds, etc.

FIG. 1 shows a laser 11 operable to generate a laser beam B at output 12 and direct the beam to impinge upon a select area WA of a surface WS1 of a substrate W1 which may define a solid material, a coating, a liquid or a liquid containing solids. The substrate or liquid W1 may be moved along a conveyor, through a duct or conduit or carried in one or more directions such as indicated by arrow A and perpendicular to the plane of FIG. 1, by a manipulator or machine, past laser 11. Laser 11 may also include a mirror M (see FIG. 1a), prism or lens which is controllably deflected or pivoted about a pivot P to cause beam B to scan a select path such as a line, raster, spiral or other path across the surface WS1 while the substrate is stationary or in movement. Mirror M (or a prism or lens—not shown) may also be synchronously pivoted in mutually perpendicular directions about mutually perpendicular or otherwise extending axes. To perform a scan, the sample may be indexed in one (X) direction and the mirror may scan in a mutually perpendicular (Y) or other direction. The specimen may be mounted on a stage.

A computer 18 generates and applies control signals or codes to a controller 13 for operating laser 11, which signals may be in the form of a code or a series of codes operable to variably control the duration, timing, intensity and in certain applications, the wavelength or frequency of the radiation defining beam B in accordance with a scanning program or cycle and/or with feedback signals applied to the control computer 18 and derived from the output of a sensor, such as a photoelectric detector 15, disposed or supported adjacent laser 11 and operable to detect radiation defined by reflections of the radiation of beam B, reflections thereof less absorbed radiation and/or fluorescent radiation caused when the matter intersected by the beam is excited thereby to fluoresce. Detection may be performed by a sensor or sensors responsive to intensity, wavelength, or frequency of the electro-optically sensed radiation. Reflected beams or fluorescent radiation from the specimen may be examined wherein the sensor 15 is part of an electronic spectrometer.

The input 16 to the photoelectric detector 15 may include a deflectable or pivotable mirror which is motor operated to permit the receipt of reflected and/or fluorescent radiation generated by the beam B and intersecting the surface WA and/or matter therebelow.

Figure 1A:
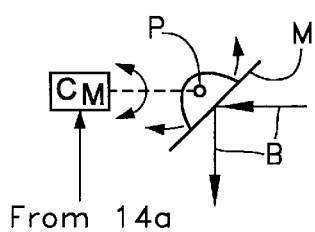
FIG. 1a is a simplified schematic drawing showing a mirror deflection technique for use in the embodiment of FIG. 1.

In the embodiment of FIG. 1a, computer 18 is capable of generating control signals 14a for operating the control motor $C_M$ for pivoting mirror M shown in FIG. 1a. Two such motors are provided to rotate mirror M in mutually different or perpendicular directions.

Figure 2:
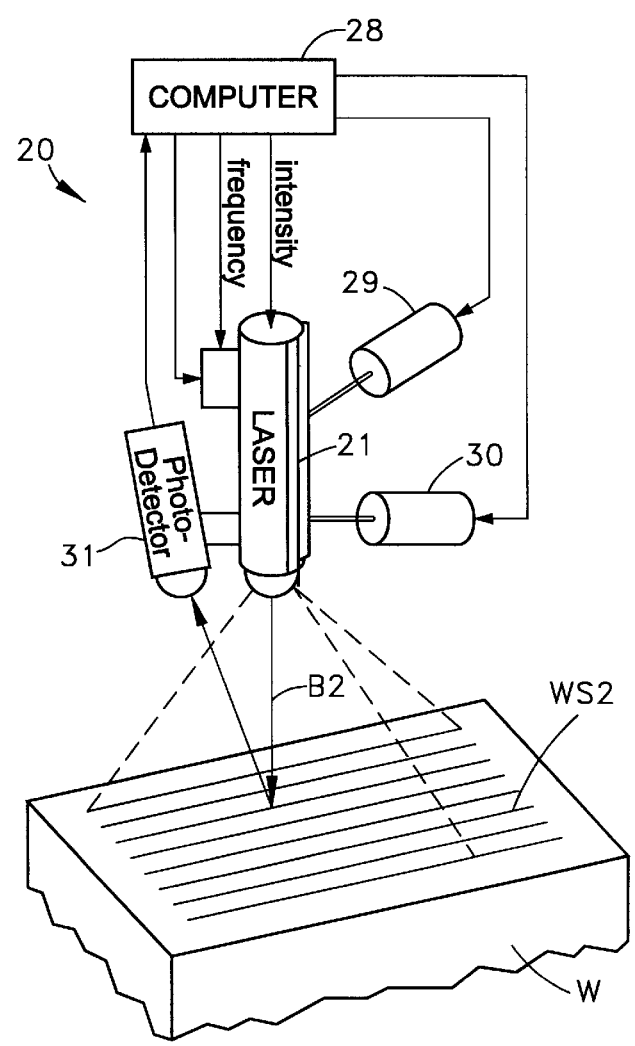

In FIG. 2 is shown a scanning system 10 operable to scan a select path, such as defined by a raster scan (or a spiral scan, if desired), across a surface WS2 of a specimen, skin, tissue, or object W2 or a volume defined by a closed (transparent) container or open container or chamber, to automatically detect (select) variations therein, such as variations in the composition of matter such as molecules, chemicals, biochemicals and/or other biological matter which may vary across the surface scanned and/or in the volume scanned, to quantize and/or locate select variations in or select portions of such matter. Laser 21 is operable to generate an output beam B2 under the control of computer 28 wherein signals from the computer cause the beam to perform a raster scan or other type scan over a select surface portion or volume of a scan field. Such field scanning may be effected one or more times by computer controlling two motors 29 and 30 to control and effect the X and Y directional deflection of a mirror (see FIG. 1a) or other optical device, such as a prism, operable to receive the laser generated beam B2 and direct the beam along a select scanning path across the surface WS2.

In a preferred form, computer 28 is operable to generate control signals, such as codes provided at a plurality of outputs to control the operation of the laser 21 and the beam or mirror deflection devices 29 and 30 (which may be motors or force transducers such as piezo-electric devices) which operate in synchronism to deflect the beam B2. Beam B2 may be operated in an on-off mode (i.e. pulsed), at a fixed frequency or may be varied in frequency (or wavelength) in accordance with the computer program or feedback signals fed to the computer 28 from one or more sensors such as spectrometers, photoelectric cells or photodetectors 31 and/or one or more computers analyzing the signals generated thereby in sensing select radiation generated or caused by the beam B2 as it scans. The reflected beam or fluorescent radiation derived from the specimen may be examined in a variety of ways including computer analysis of signals indicative of wavelength and/or intensity, angle of reflection or fluorescence, etc. generated by the use of appropriate sensors.

Figure 3A:
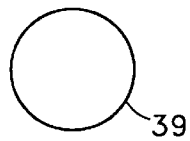
FIGS. 3a and 3b show end views of devices for use in the embodiment of FIG. 3.
Figure 3B:
Figure 3:
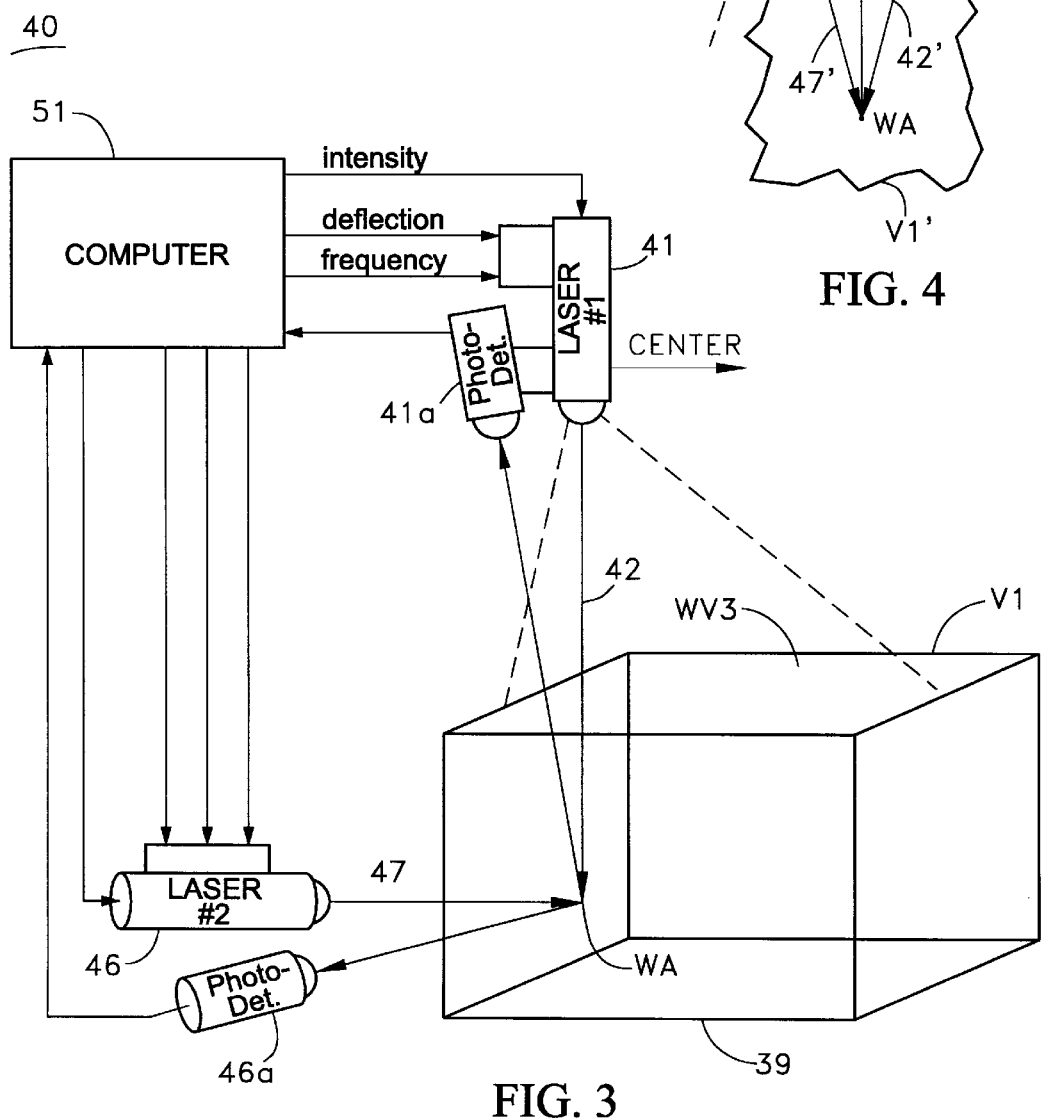

FIG. 3 shows a scanning system 40 operable to scan and detect select matter, cells, molecules or the like in a volume V, such as the interior of a container or duct 39 which may be tubular in shape or may be open at the top (see FIGS. 3a and 3b) or an ambient volume such as a portion of the atmosphere. Two lasers 41 and 46 are arranged on a suitable support (not shown for purposes of simplicity) and spaced apart from and arranged transverse to each other, and have respective outputs 42 and 47, each of which contain a multi-direction (X,Y) or (X, Y, Z) deflection control system for each of the laser beams generated by lasers 41 and 46. Lasers 41 and 46 are each preferably of the tunable type and each is provided with a respective frequency or wavelength varying input controller respectively denoted 43 and 48 which responds to digital or analog output signals generated by the controller or computer 51. The tunable lasers may, for example, be of the type described in the article "Dye-Laser Alternative Cover the Spectrum" appearing at pages 69–76 in the September 1994 issue of Laser Focus World.

Figure 4:
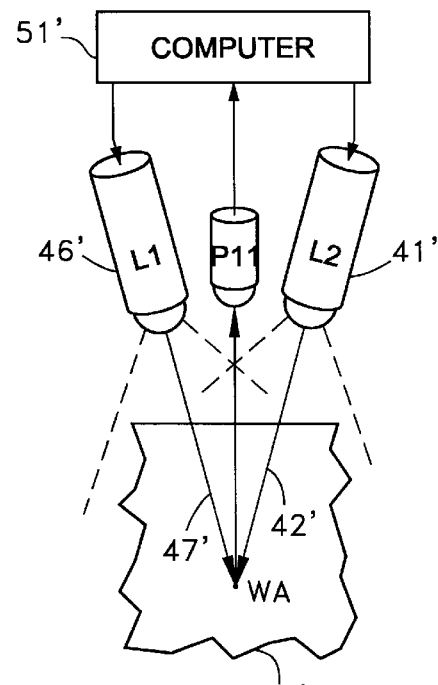

While lasers 41 and 46 are shown supported respectively above and to one side of volume $V_1$ permitting the beams 42 and 47 of each laser to scan and intersect substantially at a right-angle (or greater or less than a right-angle) to each other, lasers 41 and 46 may also be mounted next to each other, as shown by lasers 41' and 46' in FIG. 4, and operable to scan with the beams 42' and 47' thereof intersecting within volume $V_1$ disposed at acute angles to each other as shown.

The lasers 41 and 46 (and 41' and 46') of FIGS. 3 and 4 may be controlled in their operations to automatically scan the fluid, molecules or particles or a fluid containing solid particles in volume $V_1$ (or $V_1'$) along a plurality of layers or stratum therein within which layers the two beams intersect during the scanning of such respective layers so as to impose on the molecules or matter of each layer the combined effect of the two intersecting beams of radiation. By employing this scanning method, matter or molecules in each layer and in the entire volume so scanned by the two beams may be analyzed and/or reacted on by the combined effect of the radiation of the two intersecting beams. In other words, each of the two intersecting beams of radiation may be generated at an intensity (and frequency) such that when they intersect (in volume V), they will generate and direct radiation to matter or molecule(s) at the point or area of intersection which impinging radiation, (i.e. the total of the radiation beams 42 and 47) is sufficient to excite the matter or molecules within such area to fluoresce and/or to reflect same to the exclusion of other matter or molecules along the path of the respective beams other than at the area of intersection thereof. Thus all or a selected portion(s) of volume $V_1$ (or $V_1'$) may be scanned in a three-dimensional scanning operation in which the total volume scanned is divided into a series of separate sheet-like volumes or slices thereof by (computer) deflection controlling the two beams to intersect as they respectively scan within each sheet-like or layer-like volume. Such intersections of the two beams may define raster-like scans within each sheet-like volume which may be substantially repeated from one sheet-like or layer-like volume to the next (therebelow).

If the scanning beam or beams are each controlled in deflection by digital code signals which define or are proportional to coordinate locations of the beam, or two intersecting beams, in the field or volume scanned, the code signals (and/or timing signals generated from the start of scanning) may be employed to indicate the location of the areas intersected by the two beams when select matter or molecules are detected, if it is required to locate and/or quantize such select matter in the volume ($V_1$) scanned. For example, if the two beams are generated at an intensity and/or wave length or frequency wherein the combined effect of both beams on matter at the location of intersection is such as to cause such matter to become excited to fluorescence to the exclusion of other matter intersected by one beam but not the other, then the scanning intersection of the two beams may be employed to investigate or to excite or change matter at select locations within volume $V_1$ and/or just at those locations where select matter exists.

Where system 40 (FIG. 3) is employed to investigate and intelligibly indicate the presence of select matter or molecules in a given volume containing a liquid or gas, system 40 may be operated to detect select matter, quantize or operate on such matter with radiation or to define what matter it detects and operate on or remove selected matter thereof. In a particular form, the system 40 may be employed to destroy select bacteria, virus or cancer cells in tissue or body fluid such as blood, with the radiation of the intersecting beams. The system 40 may also be employed to record digital data in a solid material by using the radiation of the intersecting beams to chemically and/or physically change matter in the spot-like areas intersected by the two beams, in a pulsed operation and to reproduce select information from such record media 30. Also 3D modelling using radiation curable (by the combined radiation of the intersecting beams) photopolymers may be so effected as described above.

Figure 5:
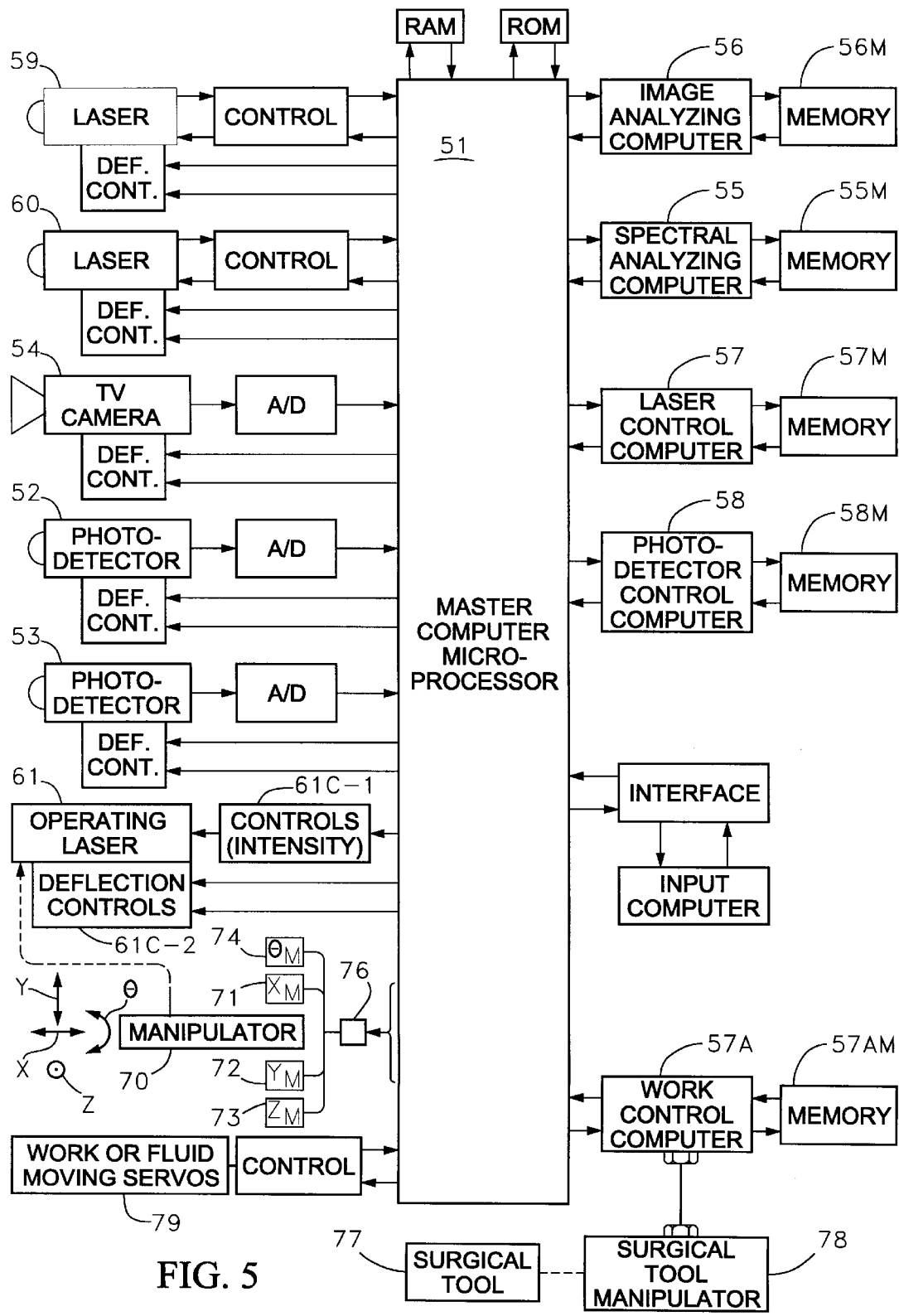
FIGS. 5 and 6 are block diagrams showing different embodiments of computer systems and controls for operating the laser devices shown in FIGS. 1–4.

FIG. 5 is a schematic diagram of a system 50 for automatically controlling the operation of electro-optical scanning apparatus of the types shown in FIGS. 1–4. A master computer or microprocessor 51 synchronizes and controls communications between a television camera 54, one or more electro-optical scanners 52, 53 and spectral and image analyzing computers 55 and 56 respectively, which process and analyze signals generated by the scanners in accordance with information recorded in their memories 55M and 56M and generate respective trains of code signals. Such code signals are passed to a laser control computer 57 and a photodetector control computer 58, each having a respective memory 57M, 58M, and which generate control codes for controlling the operations of the laser 59, 60 and TV 54 scanners and photodetectors 52, 53.

System 50 includes an operating laser 61 and controls 61C-1, 61C-2 therefor which control its operation to cause it to controllably scan and radiate or treat, ablate or destroy select matter such as cancerous tissue detected by the scanners. An automatic manipulator 70 reciprocally movable along directions X, Y, Z and $\theta$ is operated by a plurality of reversible gear motors 71–74 and positions and moves treatment laser 61 to permit it to predeterminately operate on select tissue or matter in accordance with command control signals generated by a manipulator control computer 76 which receives and analyzes signals generated by computers 55, 56 through master computer 51. The operating laser 61 may be replaced by one or more powered surgical tools 77 operated under control of a tool manipular 78 and computer 57A in accordance with signals generated by computers 55, 56 and coupled thereto by master computer 51.

Fluids are moved by pumping or by solenoid operating or moving a valve under control of servos 79, control circuits 79A and computer 57 through master computer 51.

Figure 6:
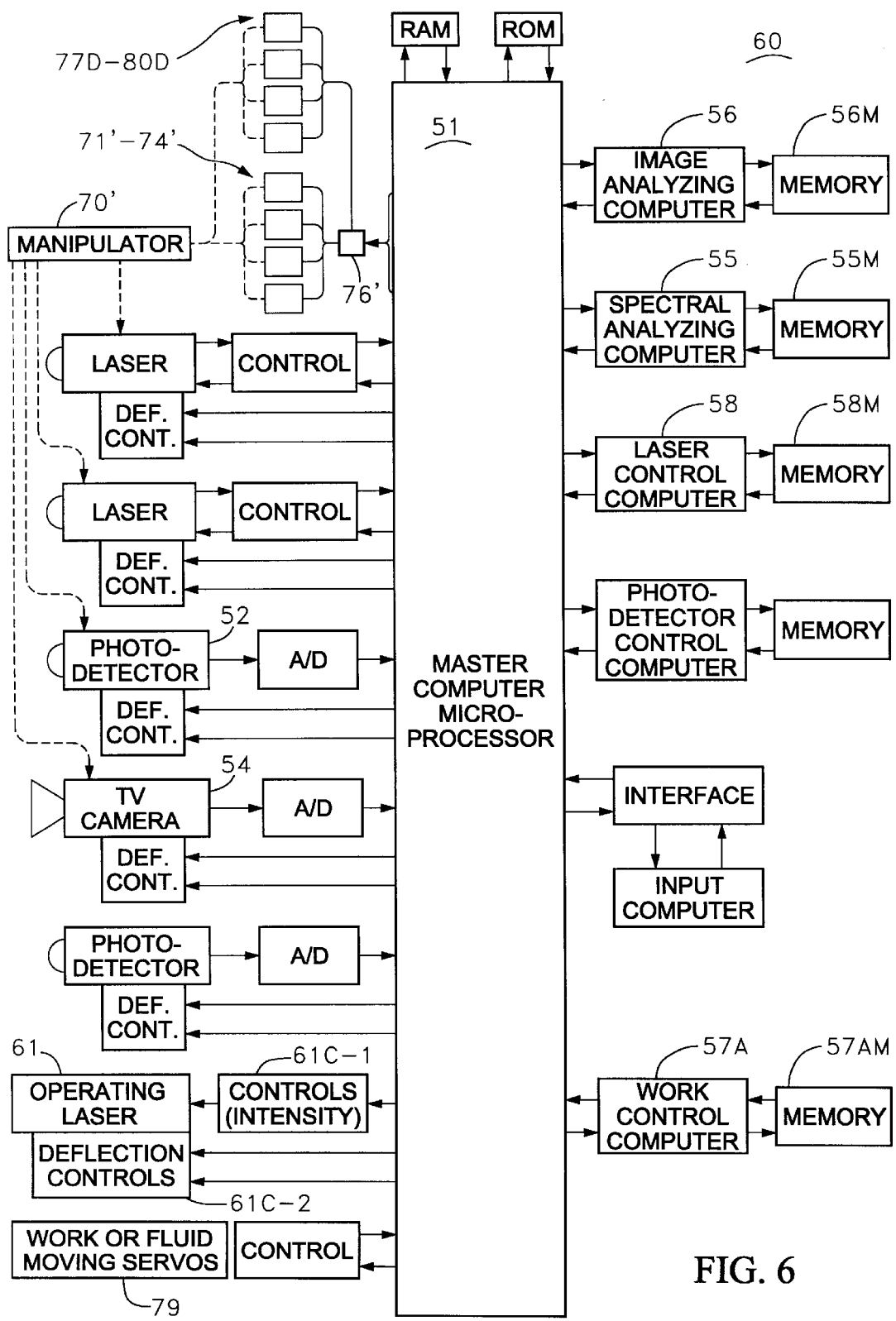

FIG. 6 shows a modified form of the invention defined by a system 60 employing one or more automatic manipulators 70' for positioning the scanning and photoelectric detecting devices and subsystems of FIGS. 1–5 to either preposition same with respect to a living being or object prior to a computer controlled scanning operation and/or to effect an automatic computer controlled electro-optical scanning operation after such prepositioning. The system 60 of FIG. 6 may employ substantially all or some of the devices and subsystems shown in FIG. 5 including one or more lasers supported by one or more manipulator arm assemblies defining or forming part of one or more computer controlled manipulators. The arm assemblies of such manipulator(s) are driven by a plurality of reversible gear motors 71'–74' each containing a respective shaft digitizer 77D to 80D for generating feedback codes which are applied to manipulator control computer 76' for operating the motor(s) in a feedback control mode.

The TV camera 54 may also be supported by the manipulator and is operable to scan its field including the image of the patient or object to be inspected and generates image signals which are digitized and analyzed by image analyzing computer 56 which generates coded control signals in accordance with the information analyzed in that portion of the image field scanned. Such control signals are employed to (a) preposition the manipulator (S) 70, 70', etc. with respect to a select portion of the object or person to be scanned; (b) controllably operate the manipulator and one or more electro-optical scanners such as one or more lasers of the type described, one or more photodetectors, and/or the TV camera 54; (c) controllably operate one or more motors for effecting further scanning operations; and (d) controllably operate one or more motors or devices employed to further operate on the person or object inspected in accordance with the information derived from computer analysis of the image signals derived from such automatic scanning.

Figure 7:
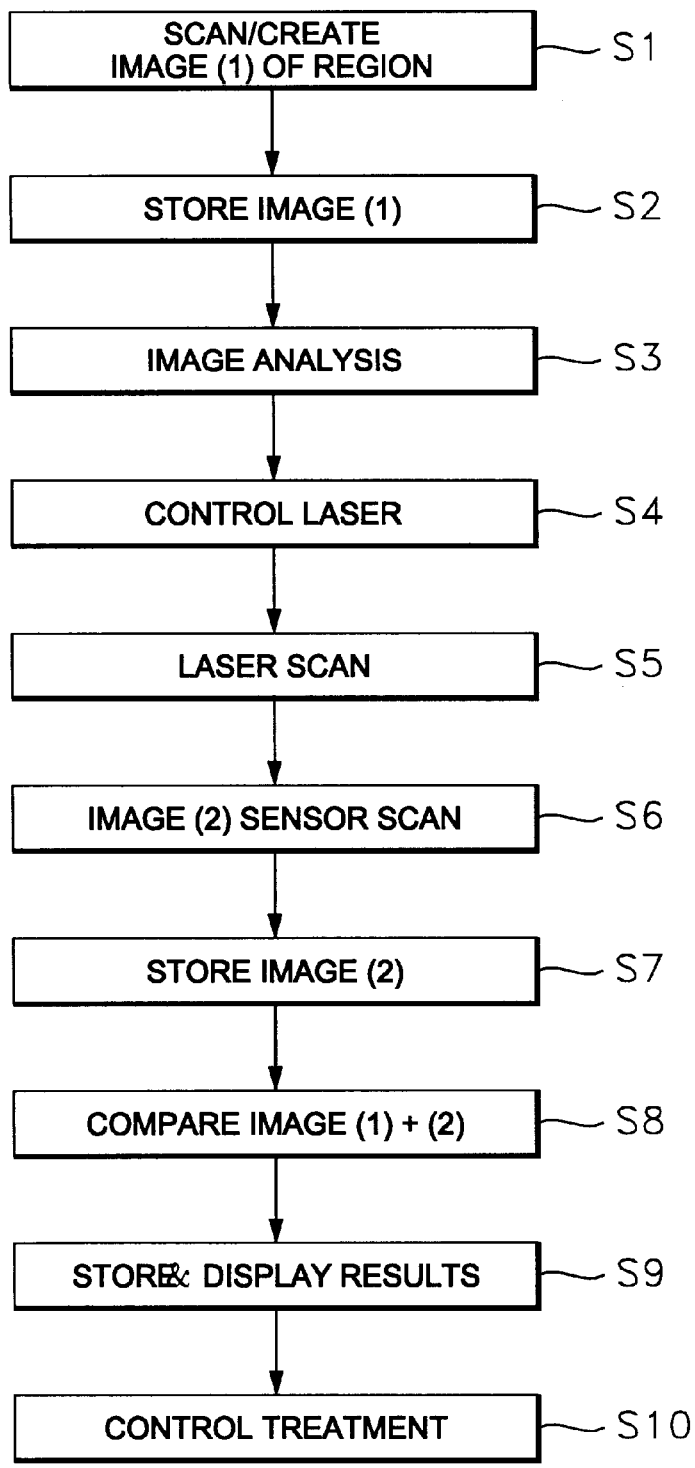
FIG. 7 is a flow diagram showing the manner of computer operation of the various embodiments of the present invention.

FIG. 7 is a flow diagram which is useful in describing the various operations capable of being performed with the apparatus and system of the present invention.

Noting FIG. 7, a cycle is initiated wherein, in method step S1 an image of the region to be analyzed and/or treated is created and, through the use of the TV camera, image signals are generated which image signals are digitized and stored at S2. At S3 the stored image signals are analyzed and a tunable laser is operated at S4 to generate a laser beam of a predetermined: wavelength, frequency, intensity, etc. Also the laser beam wavelength, intensity, frequency, etc. may be varied during scanning or may be controlled to scan different portions of a region at different wavelengths, frequencies or intensities.

At S5, the region is scanned by the beam of laser radiation. At step S6 the signals output by the sensors are examined, and employed to create a second image, the digitized signals of which are likewise stored at S7. At step S8 the first and second image signals are transferred from storage and are compared and analyzed to ascertain information regarding aspects of the examined region such as the presence of a tumor, the stage of a cancer if a cancerous growth is detected, the extent and shape of the malignant region or tumor, etc. At S9 the analyzed information is stored and outputted (i.e. display and/or printout).

In the flow diagram of FIG. 7, the information derived at step S8 may then be used to control and/or direct, at step S10, a beam of laser radiation for treating the malignancy. Alternatively, the operation may be such as to control and manipulate an instrument or a surgical tool to inspect or operate on select tissue (by operating motors, solenoids, valves, or the like).

The control at step S1 may be employed to operate one laser 11 as shown in FIG. 1 or a pair of lasers 41 and 46, as shown in FIG. 3.

The sensors may be the opto-electric device 15 (or devices 41a, 46a of FIG. 3) or a spectrometer or other like instrument.

The sensing operation may examine amplitude or intensity of a reflection or a fluorescence, wavelength or frequency, angle of reflection or radiation.

The control of radiation at step S1 and/or S5 may also include controlling a flow of a fluid (such as blood) when it is a fluid that is being examined, or may control moving a body, a tissue or other matter when such matter is being examined, in addition to laser beam control.

Steps S1 and S5 may further include controlling the interval or intervals that a beam is on.

Timing means is activated as a substep of steps S1 and/or S5 when required to identify a location or locations of a particular condition or site from a given reference or starting point from which a beam originates and then moves to said site.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A method of electro-optically scanning matter within a given region comprising the steps of:
   (a) generating a first beam of radiation;
   (b) directing said first beam of radiation into said matter;
   (c) generating a second beam of radiation;
   (d) directing said second beam of radiation into said matter so that the second beam of radiation intersects with the first beam of radiation at a location within said matter to excite said matter at said location, said first and second beams of radiation intersecting at a given angle;
   (e) photoelectrically detecting the excited location and generating first variable electrical signals;
   (f) digitizing said first variable electrical signals and generating first digital code signals;
   (g) spectrally analyzing said first digital code signals with a computer and generating second code signals; and
   (h) employing said second code signals to intelligibly indicate a presence of a constituent in said matter at said location.

2. The method of claim 1 wherein said angle is an acute angle.

3. The method of claim 1 wherein said angle is a right angle.

4. The method of claim 1 wherein step (f) further comprises determining if said constituent is a type of molecule.

5. The method of claim 1 wherein step (f) further comprises determining if said constituent is a given material.

6. The method of claim 1 wherein step (f) further comprises determining if said constituent is a given element.

7. The method of claim 1 wherein step (f) further comprises determining if said constituent is a diseased element.

8. The method of claim 1 wherein step (f) further comprises determining if said constituent is a cancerous element.

9. The method of claim 1 further comprising moving said first and second beams so that said first and second beams cooperatively scan at least a given portion of said fluid.

10. The method of claim 9 further comprising the step of generating time code signals during scanning and employing said time code signals to indicate a location in the scan.

11. The method of claim 1 wherein said matter is a fluid and said beams are caused to intersect at a region within said fluid.

12. The method of claim 11 wherein said fluid is blood and said beams are caused to intersect at a region within said fluid.

13. The method of claim 11 wherein said fluid is a gas and said beams are caused to intersect at a region within said fluid.

14. The method of claim 11 wherein said fluid is a liquid and said beams are caused to intersect at a region within said fluid.

15. A method of electro-optically scanning matter within a given region, comprising the steps of:
   (a) generating a first beam of radiation;
   (b) directing said first beam of radiation into said matter;
   (c) generating a second beam of radiation;

(d) directing said second beam of radiation into said matter so that said second beam of radiation intersects with the first beam of radiation at a location within said matter to excite matter at said location;

(e) controlling the intensity of said beams so that a sum of radiation of said beams is sufficient to excite said matter at said location while the radiation of the individual beams is insufficient to excite the matter at said location.

16. The method of claim 15 wherein said sum of said radiation of said beams is sufficient to cause the matter at said location to fluoresce.

17. The method claim 15 wherein said first and second beams are each scanned in at least two mutually perpendicular directions.

18. The method of claim 15 wherein said first and second beams are each scanned in at least three mutually perpendicular directions.

19. The method of claim 15 wherein said sum of said radiation is chosen to destroy matter at said location.

20. The method of claim 19 wherein said matter includes one of bacteria, virus and cancer cells.

21. The method of claim 15 further comprising:

(a) photoelectrically detecting the excited location and generating first variable electrical signals;

(b) digitizing said first variable electrical signals and generating first digital code signals;

(c) spectrally analyzing said first digital code signals with a computer and generating second code signals; and (d) employing said second code signals to intelligibly indicate a presence of certain matter at said location.

22. A method of treating matter, comprising the steps of:

(a) generating a first beam of radiation;

(b) directing said first beam of radiation into said matter;

(c) generating a second beam of radiation;

(d) directing said second beam of radiation into said matter so that the second beam of radiation intersects with the first beam of radiation at a location within said fluid to excite said matter at said location; and (e) controlling the intensity of the first and second beams of radiation so that their sum is sufficient to record digital data in said material.

23. A method of treating matter, comprising the steps of:

(a) generating a first beam of radiation;

(b) directing said first beam of radiation into said matter;

(c) generating a second beam of radiation;

(d) directing said second beam of radiation into said matter so that the second beam of radiation intersects with the first beam of radiation at a given angle and at a location within said matter to excite said matter at said location; and (e) controlling radiation intensity of said first and second beams of radiation to chemically change matter at the location intersected by said first and second beams of radiation.

24. The method of claim 23 wherein said matter is a radiation curable photo-polymer and said photo-polymer is cured at said location by a sum of said first and second beams of radiation.

* * * * *